US008292851B2

(12) United States Patent
Ferrari

(10) Patent No.: US 8,292,851 B2
(45) Date of Patent: Oct. 23, 2012

(54) RADIALLY EXPANDABLE ANCHOR GUIDE FOR A TROCAR

(75) Inventor: Danilo Ferrari, Arezzo (IT)

(73) Assignee: AB Medica S.p.A., Lainate (MI) (IT)

( * ) Notice: Subject to any disclaimer, the term of this patent is extended or adjusted under 35 U.S.C. 154(b) by 754 days.

(21) Appl. No.: 11/919,648

(22) PCT Filed: Apr. 26, 2006

(86) PCT No.: PCT/IT2006/000283
§ 371 (c)(1),
(2), (4) Date: Oct. 29, 2007

(87) PCT Pub. No.: WO2006/117819
PCT Pub. Date: Nov. 9, 2006

(65) Prior Publication Data
US 2009/0318866 A1    Dec. 24, 2009

(30) Foreign Application Priority Data
Apr. 29, 2005    (IT) .................. FI2005A0082

(51) Int. Cl.
*A61M 5/178* (2006.01)
(52) U.S. Cl. .................................. 604/164.04
(58) Field of Classification Search .......... 604/164.04
See application file for complete search history.

(56) References Cited

U.S. PATENT DOCUMENTS

| 3,789,852 | A |   | 2/1974  | Kim et al. ............... 128/347 |
| 5,431,676 | A | * | 7/1995  | Dubrul et al. ............ 606/185 |
| 5,437,644 | A | * | 8/1995  | Nobles ................. 604/164.11 |
| 5,697,913 | A | * | 12/1997 | Sierocuk et al. ....... 604/164.11 |
| 5,871,474 | A |   | 2/1999  | Hermann et al. ......... 604/256 |
| 6,110,154 | A |   | 8/2000  | Shimomura et al. ...... 604/256 |
| 6,589,167 | B1 |  | 7/2003  | Shimomura et al. ...... 600/208 |
| 2004/0215063 | A1 | | 10/2004 | Bonadio et al. ........... 600/201 |

FOREIGN PATENT DOCUMENTS
GB          330629 A    6/1930
WO    WO 9952577 A1   10/1999

* cited by examiner

*Primary Examiner* — Nicholas Lucchesi
*Assistant Examiner* — Aarti B Berdichevsky
(74) *Attorney, Agent, or Firm* — Pollack, P.C.

(57) ABSTRACT

An anchor guide for a trocar comprising a tubular body, formed by a plurality of substantially circular sectors, moveable radially toward and away from a longitudinal axis of the tubular body between a first position where they flank one another, according to a first substantially circular arrangement with diameter generally equal to that of the tubular body, and a second position at which they are generally equidistant from one another, according to a second substantially circular arrangement of greater diameter than that of the first arrangement. Each sector is rotatably connected to a support element and a manual operation member is provided, moveably connected to the support element, for moving the sectors from the first to the second position and vice versa.

12 Claims, 5 Drawing Sheets

RADIALLY EXPANDABLE ANCHOR GUIDE FOR A TROCAR

FIELD OF THE INVENTION

This disclosure relates generally to medical devices and, more particularly, to devices for use in laparoscopic surgery and the like.

BACKGROUND OF THE INVENTION

During laparoscopic surgery, instruments known as trocars are commonly used to generate and maintain access channels for the various surgical instruments used to perform surgical operations. Commercially available trocars usually comprise a cannula having a valve body situated at one of its ends. Typically, the cannula has a diameter of about 5 mm or about 12 mm with a length generally within a range of 110mm and 120 mm.

Upon commencement of the surgical operation, the surgeon makes incisions or holes, for example, in the abdomen of the patient, using a corresponding number of trocars each equipped with an accessory for penetrating the various layers of abdominal tissue. Subsequently, each such accessory is extracted and the abdomen is insufflated with an inert gas through one of the trocars so as to generate the desired amount of operating space in the abdominal cavity.

Since the pressure generated inside the patient's abdomen tends to push the trocars outwardly, various methods have been devised to anchor trocars during use. The most common approach utilizes a tube with an inner diameter equal to the outer diameter of the trocar cannula. The tube is also provided with an outer threaded surface which enables the surgeon to "screw it" into the access hole. The tube is then secured to the cannula of the trocar using elastic bands or other friction based systems.

During surgery, all of the necessary instruments are inserted through the trocars. In procedures where internal organ parts or tissue must be removed, for example, gall bladder, intestine parts, tumoral masses, etc., it may necessary to make further incisions in the patient's abdomen of sufficient size to allow passage of the part or tissue to be removed. This often warrants creating additional wounds in the abdomen of greater size than those left by the trocars, with the possibility of contamination through the walls of the incision made during extraction of the parts or tissue hindering post operative recovery of the patient. Morover, as laparoscopic surgical procedures often continue after the extraction step has been performed, and given that the additional incision necessary for extraction may compromise the gas seal, special instruments must often be used to restore the seal.

OBJECTS AND SUMMARY OF THE INVENTION

Accordingly, it is an object of this disclosure to provide an anchor guide for a trocar that takes advantage of elasticity of anesthetized tissues, which are relaxed, by expanding them so as to generate the space necessary for extracting any organ part or tissue to be removed during the surgical procedure without the need for additional surgical incisions.

It is another object of the the disclosure to provide an anchor guide for a trocar suitable for mounting an autonomous valve system through which instruments or an adaptor for commercial trocars can pass, should it become necessary, after extraction of organ parts or tissues, to re-pressurize the abdomen and restart the operation.

According to one aspect of the disclosure, an anchor guide is provided for a trocar for use in laparoscopic surgery. The guide comprises a tubular body with a member for its anchorage to an access hole for entering a body cavity, wherein the tubular body is formed by a plurality of substantially circular sectors. The sectors are rigid along a circumferential direction of the tubular body and moveable radially toward and away from a longitudinal axis of the body between a first position, where they flank one another according to a substantially circular first arrangement of diameter generally equal to that of the tubular body, and a second position, at which they are generally equidistant from one another according to a substantially circular second arrangement of greater diameter than that of the first circular arrangement. The plurality of sectors are rotatably connected to a support element and a manual operation member, moveably connected to the support element, for moving the sectors from the first to the second position and vice versa.

BRIEF DESCRIPTION OF THE DRAWINGS

A specific, illustrative anchor guide for a trocar, according to this disclosure, is described below with reference to the accompanying drawings, in which.

The same numerals are used throughout the drawing figures to designate similar elements. Still other objects and advantages of the disclosure will become apparent from the following description of the preferred embodiments.

DETAILED DESCRIPTION OF THE PREFERRED EMBODIMENTS

Figure 1:
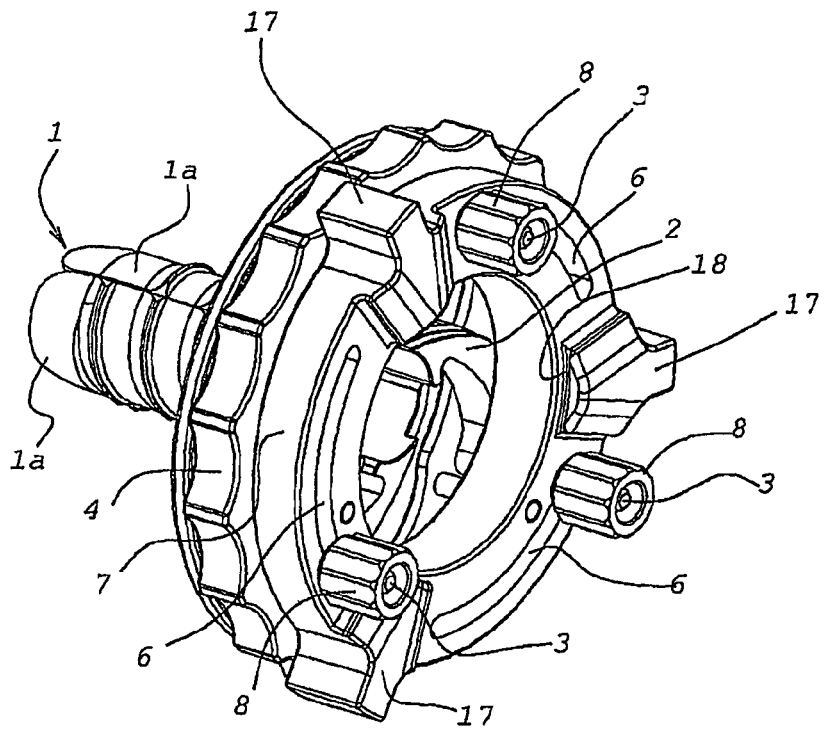
FIG. 1 is a perspective view of an anchor guide, according to one aspect of the disclosure, in a closed position.
Figure 2:
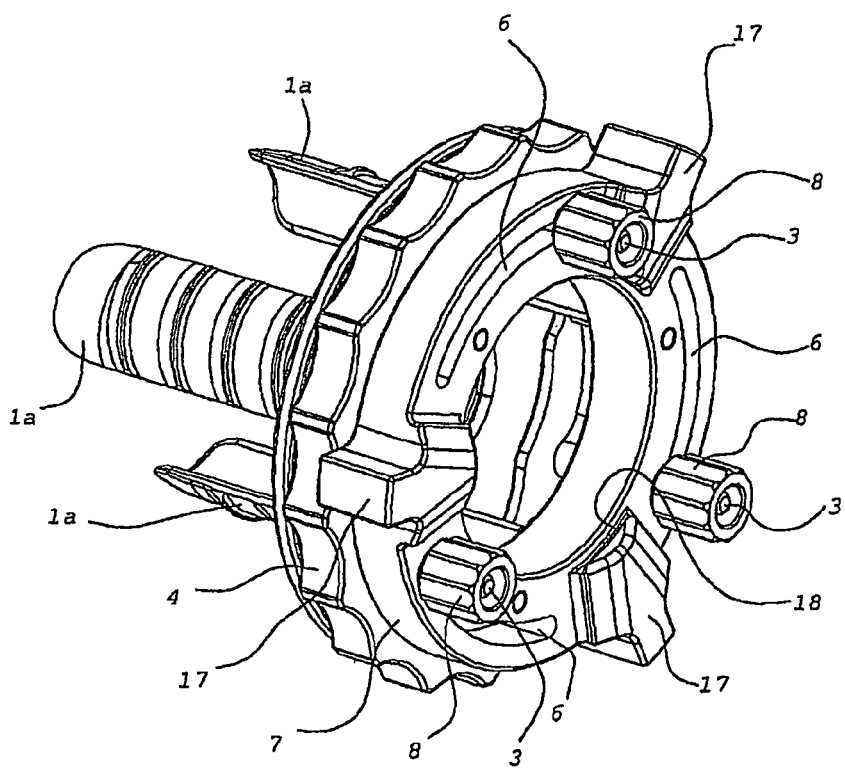
FIG. 2 is a perspective view of the anchor guide set forth in FIG. 1 in an open position.
Figure 3:
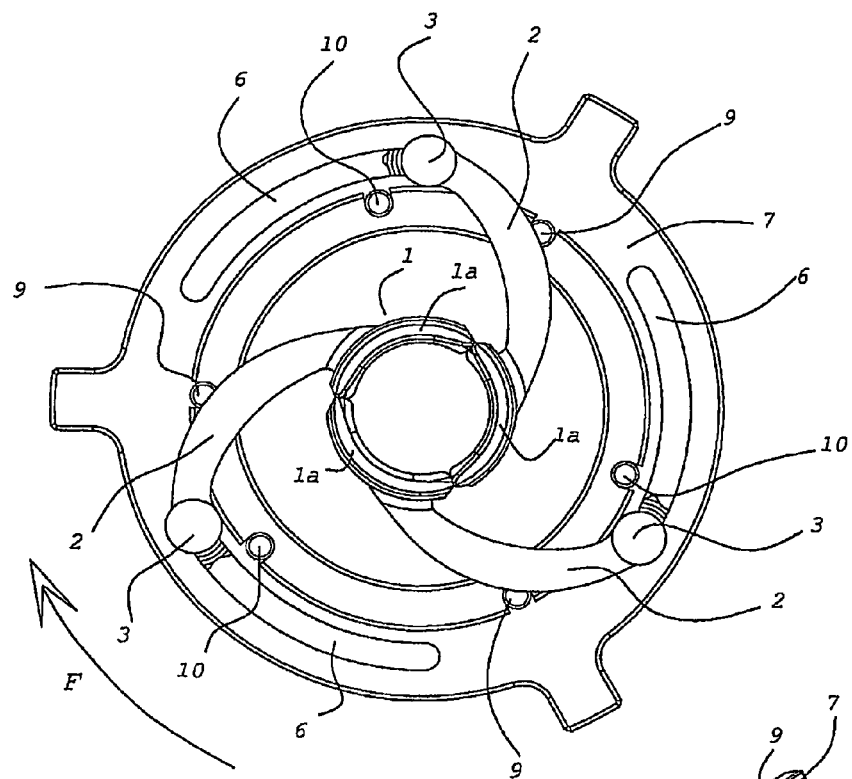
FIG. 3 is a sectional view of the anchor guide illustrated in FIG. 1.

Referring now to the drawings and, more particularly, to FIGS. 1-4, there is shown generally a specific, illustrative anchor guide for a trocar, according to various aspects of the disclosure. In one example, illustrated generally in FIG. 1, the trocar has a tubular body 1 is formed by three sectors 1a of angular width generally equal to about 120°. From one end of each of sectors 1a, a curved arm 2 extends in a substantially tangential manner; a free end of the curved arm being rotatably engaged with a pin 3. The three pins are, in turn, engaged with three equidistant holes 5, respectively, formed in a first ring nut 4, referred to as a fixed or stationary ring nut, orthogonal to a longitudinal axis of tubular body 1 and in circumferential slots 6 made along a second ring nut 7, known as a moveable ring nut, arranged coaxially on stationary ring nut 4. Finally, the threaded ends of the pins projecting from the slots of the moveable ring nut are engaged with respective threaded knobs 8, abutting moveable ring nut 7 and in opposition to stationary ring nut, thereby mutually securing the various components.

Cylindrical sectors 1a of tubular body 1 form a channel having an inner diameter less than or equal to an outer diameter of a cannula of the commercial trocar to be used. The outer surface of each sector has a saw tooth thread, as in conventional anchor cannulae, suitable for grasping walls of an access hole or incision in a patient's body cavity.

Curved arms 2 are housed within stationary ring nut 4, coplanarly thereto, and may be rotated simultaneously about the respective pins, so as to transmit angular movement to moveable ring nut 7. After rotation of the curved arms, cylindrical sectors 1a which extend therefrom progressively divaricate from one another, passing from a closed configuration, as illustrated in FIG. 1, to an open configuration according to FIG. 2.

Figure 4:
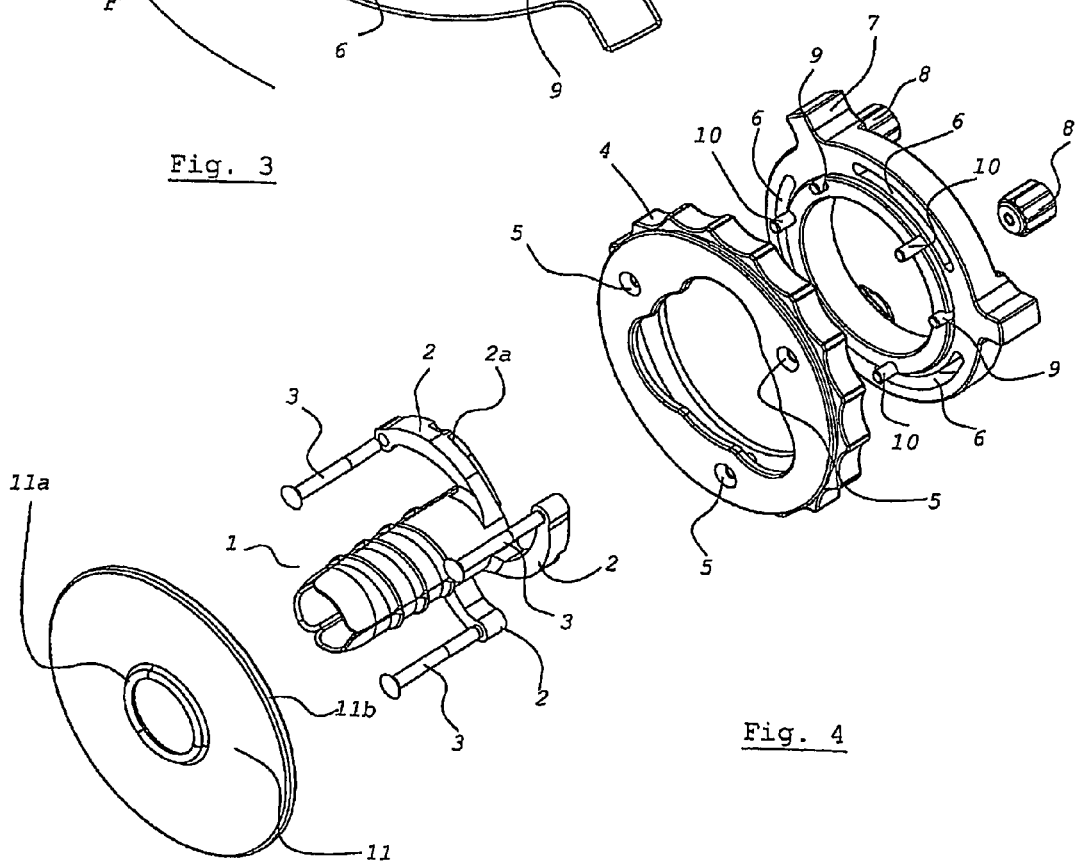
FIG. 4 is an exploded view of the anchor guide set forth in FIG. 1.

Three angularly equidistant closure pins 9 and three thrust pins 10 extend orthogonally from the face of the moveable ring nut towards the stationary ring nut. When tubular body 1 is in a closed position, as shown in FIG. 1, the closure pins abut the convex side of the respective curved arms and maintain cylindrical sectors 1a adjacent to one another, tightening them on the cannula of the trocar so as to permit axial locking of the trocar. In particular, as best seen in FIG. 4, the arms have seats 2a, for receiving and engaging closure pins 9. On the other hand, when the moveable ring nut is rotated in the direction of arrow F in FIG. 3, thrust pins 10 contact the concave profile of arms 2, sliding along the arms and away from hinge pins 3, so as to insure that the arms extend progressively. In this manner, the cylindrical sectors first open quickly, then slow as they approaches the stop end possible.

Since the resistance of body tissues increases generally with increasing divarication of the sectors, the aforementiones arrangement allows a relatively constant force to be exerted throughout the opening sep. At the stop end, the tubular body remains open and in a stable condition when the thrust pins reach the dead point. Should it become necessary to interrupt opening of the sectors in an intermediate position, it is sufficient to tighten at least one of threaded knobs 8.

Figure 5:
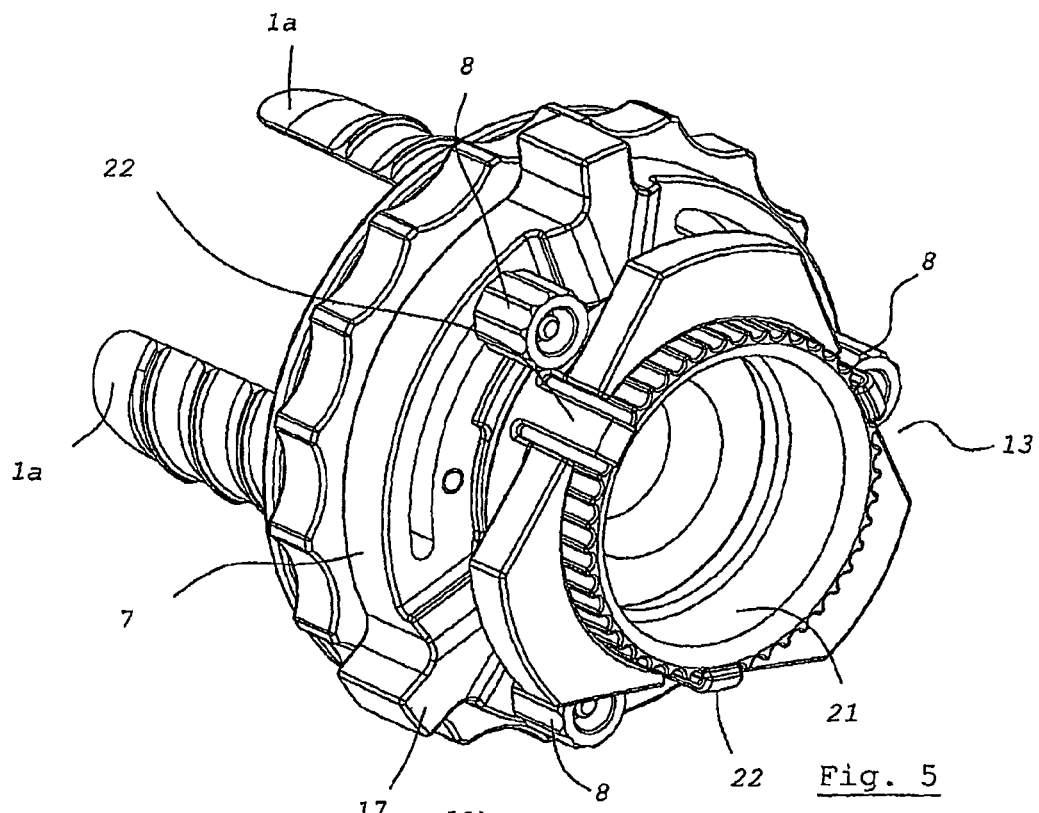
FIG. 5 is a perspective view of the anchor guide set forth in FIG. 1, in a fully open position with a diaphragm valve inserted therein.
Figure 6:
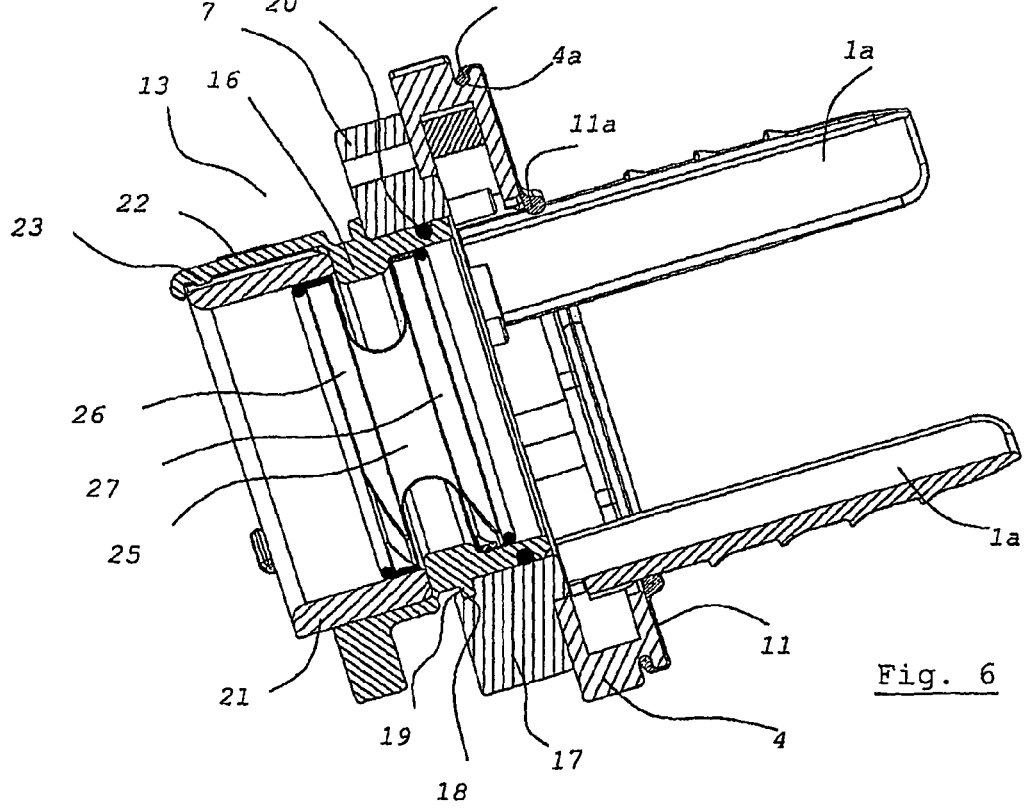
FIG. 6 is a sectional view taken longitudinally of the anchor guide shown in FIG. 5.
Figure 7:
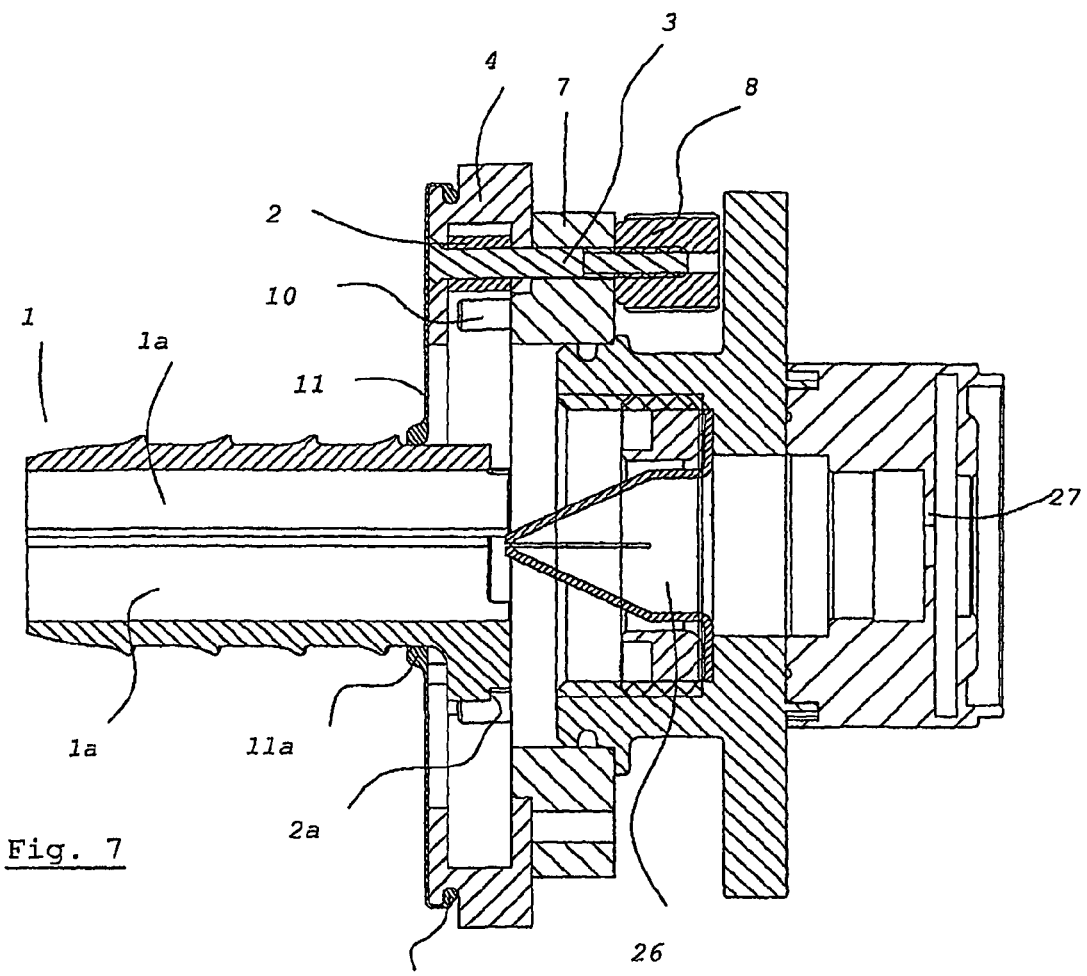
FIG. 7 is a sectional view taken longitudinally of an anchor guide, according to another aspect of the disclosure, in a closed position with a commercial valve system.

As illustrated in FIGS. 4 and 7, a membrane 11 is used to insure adequate sealing of gas in the abdomen on the patient side, whereas on the surgeon's side the seal is insured by a valve system such as that shown in FIGS. 5 and 7. The membrane has a variable thickness and, specifically, in correspondence to its minimum and maximum diameter, terminates with respective toroidal rings 11a and 11b. The maximum diameter of the rings, i.e., the ring 11b, is inserted in a perimetrical groove 4a of ring nut 4, as best seen in FIG. 6, while the minimum diameter of the rings, namely, ring 11a, is tight at the base of sectors 1a. As ring 11a is in a resting position and because the membrane is forced by the abdomen of the patient against the ring nut, the correct ring position is maintained and no groove for housing the ring is required.

The radially expandable anchor guide for trocars, according to one aspect of this disclosure, is used in the following manner. Upon commencement of the operation, during the step of inserting the trocar in the patient's abdomen, for example, the anchor guide is used as if it was a normal anchorage tube of the trocar to the abdominal wall. As set forth in FIG. 8, sectors 1a are closed around cannula 12 of the trocar and tightened thereon by rotating moveable ring nut 7 relative to stationary ring nut 4, and tightening at least one of locking knobs 8. Where the trocar inserted is calibrated according to the inner size of the closed tubular body, tightening of the locking knob can be avoided since the system is irreversible when in a fully closed position. A valve 13, of the type illustrated generally in FIGS. 5 and 6, is closed around the trocar tube to assure a perfect gas seal.

In an arrangement where a valve is used as illustrated in the drawing figures of this disclosure, it is considered unnecessary to tighten the tubular body on the cannula 12, since the same valve can provide axial anchorage of the trocar. Indeed, when the membrane tightens around the cannula, it generates a consistent radial force which, due to the high coefficient of friction between the membrane and the cannula, insures a strong axial seal.

Figure 8:
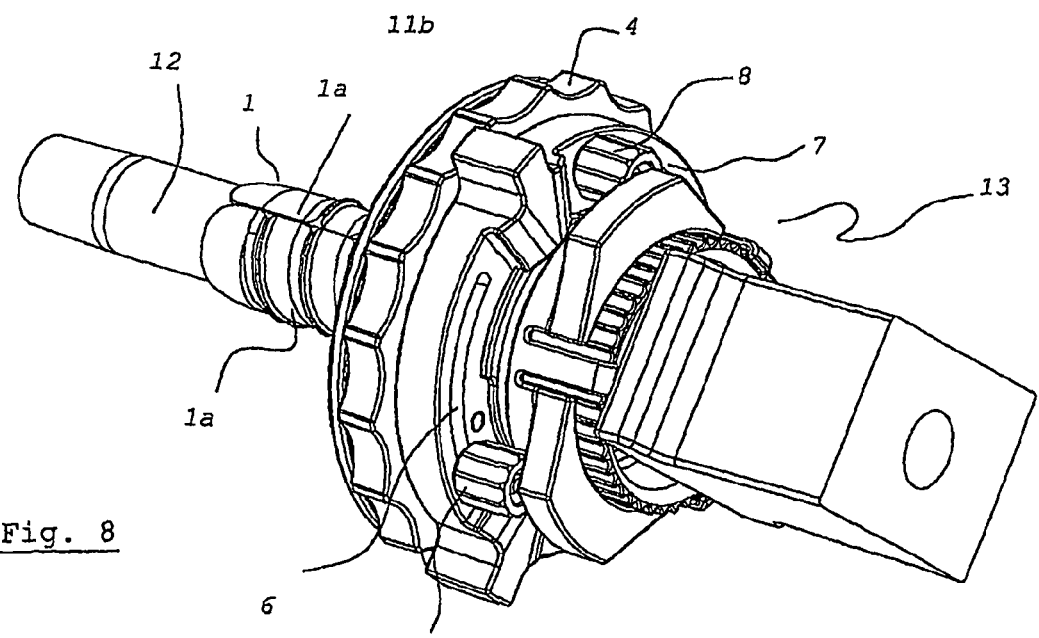
FIG. 8 is a perspective view of the anchor guide illustrated in FIG. 7 in a closed position, and equipped with a diaphragm valve having a commercial trocar housed therein.

If, during the surgical operation, it becomes necessary to insert a trocar of greater size, it is sufficient to open the valve of FIG. 8, open the tubular body by unlocking the cannula of the trocar, extract the trocar to be substituted, insert a new trocar, and then tighten the tubular body and seal valve 13 thereon.

Should it become necessary to remove an internal organ or tissue mass, the tubular body may be divaricated to its maximum expansion so that, once the trocar and the seal valve is removed, an access channel is formed in the abdomen of sufficient dimensions to allow passage of the mass to be removed.

To protect the walls of the access hole from possible contaminations (for example, during extraction of a tumoral mass where other types of protection are absent), it is possible to insert, within divaricated sectors 1a, a tube 14 (see FIG. 9) after having overturned elastic membrane 14a inside the tube itself. In particular, tube 14 comprises a rigid cylinder of thin thickness buried within an elastic membrane terminating at both ends having two large diameter discs with reinforced edges, one of which is the elastic membrane. For insertion in divaricated tubular body 1, the inner disc or membrane 14a is folded inside tube 14 and subsequently caused to expand inside the patient's abdomen. The membrane benefically protects the inner wall of the abdomen, near the access hole, from contamination. The axial position of the tube is then secured by tightening the three sectors. An outer elastic disc 15 at the other end of the tube may be folded on moveable ring nut 7 of the anchor guide so as to protect it from contamination.

Figure 9:
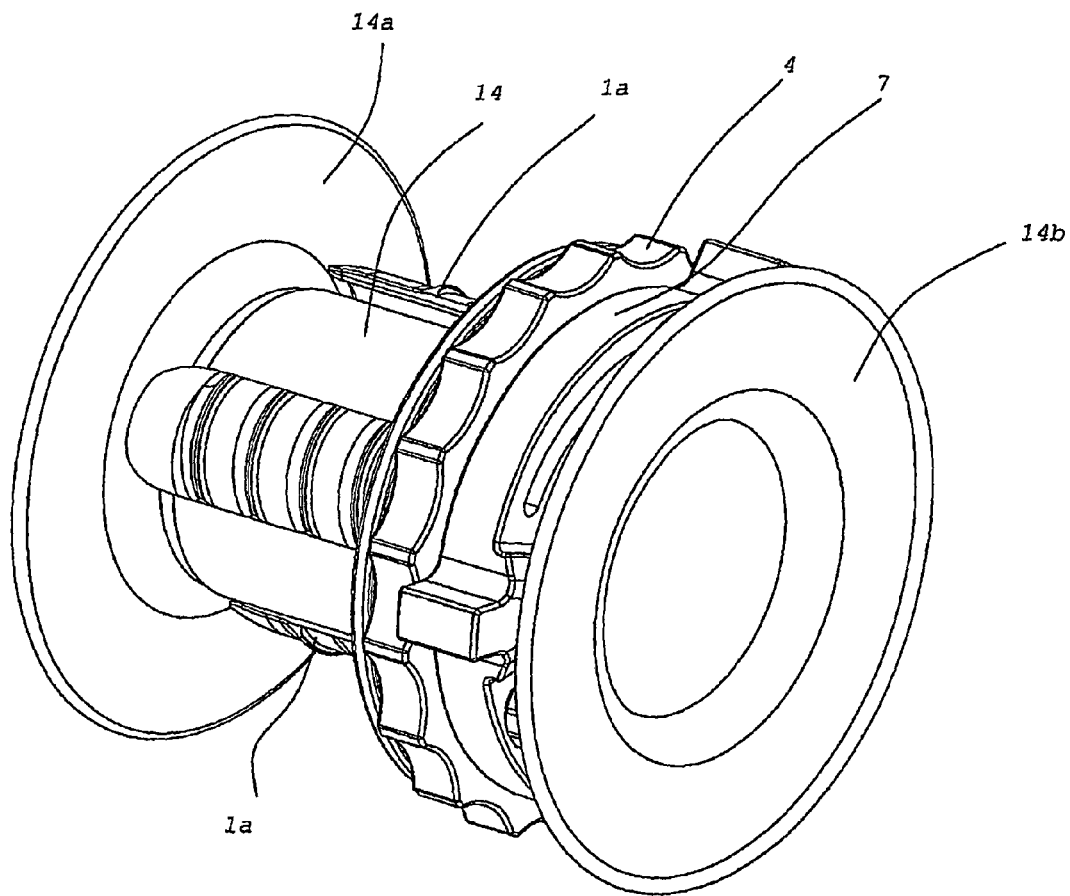
FIG. 9 is a perspective view of the anchor guide shown in FIG. 7, with a protective tube.

FIG. 9 shows an expandable anchor guide, according to another aspect of the this disclosure, in a configuration suitable for extraction of an internal organ or tissue mass. To withdraw the tube, the sectors are further divaricated, as appropriate, and the tube pulled through the outer elastic disc.

Valve 13, as illustrated in FIGS. 5 and 6, is based on the principal of operation of a commercial device commonly referred to as a "LAP-DISC", described in the U.S. Pat. Nos. 6,110,154 and 6,589,167 used for making a hole in the patient's abdomen to allow access by a surgeon's hand during hand-assisted laparoscopic surgery, even if a different method is used to maintain the set position.

With particular reference to FIGS. 5 and 6, the valve comprises a support 16 for connection via a bayonet coupling to the outer face of moveable ring nut 7. On the latter, radial expansions 17 define circumferential grooves 18 with the moveable ring nut's outer face, within which radial tongues 19, extending from the outer wall of support 16, are engaged by friction fit. A seal between the support and moveable ring nut is effected using a seal ring 20 arranged therebetween. Additionally, the valve includes a control ring nut 21 rotatably engaged within the support and maintained in a desired angular position by flexible arms 22 extending axially from the support. The flexible arms have inner radial projections 23 engaged in axial grooves 24 formed on the outer surface of control ring nut 21.

The obturator or stop of the valve comprises an elastic membrane 25 having, in a resting position, a toroidal shape with "omega" cross-section, which is maintained tightly on the inner walls of the control ring nut and support, respectively, by expansion rings 26 and 27 of rectangular section. The expansion rings are desirably cut sideways so as to permit flattening of the membrane against the walls of the control ring nut and support without formation of a gap.

Upon rotation of control ring nut 21 relative to support 16, flexible arms 22 bend, causing projections 23 to move from one groove 24 to the other, such that elastic membrane 25, due to the torsion to which it is subjected, closes radially like a diaphragm. Through appropriate rotation angle of the control ring nut, it is possible to occlude entirely the opening of valve 13, or partially occlude the opening in the event that the cannula of a trocar must pass therethrough, tightening membrane 25 around the opening, and, thereby, insuring a gas seal and consistent axial tightening.

Although the expandable anchor guide, according to this disclosure, has been shown and described herein with reference to a diaphragm valve, those skilled in the art will appreciate that other types of valves for trocars may be employed, concurrently or in the alternative, giving consideration to the purpose for which this discloure is intended. For example, trocar valves, such as the one illustrated in FIG. 7, may be utilized alternatively or concurrently, within the spirit and scope of this disclosure.

The valve illustrated herein is of a double seal type: i.e., it has a first elastic obturator 26 with a flute mouth geometry which, when at rest, is maintained in a closed position by the pressure in the patient's body cavity. Upon insertin of an instrument, the flute mouthed obturator opens correspondingly with the longitudinal cuts, though comprising the gas seal. Accordingly, a second obturator or block 27 is utilized, upstream of the first, the second obturator comprising an elastic membrane with a calibrated hole for effecting a seal with the particular instrument diameter.

Generally speaking, to insert an instrument having a different diameter, it is necessary to substitute a double obturator arrangement, namely, the second obturator secured by a bayonet coupling to the first obturator. This arrangement allows instruments to be inserted and extracted without comprising the seal, whereas, upon insertion of an instrument, the second obturator maintains a seal by pressing radially against the instrument. Although the valve system described and illustrated in FIG. 7 is considered to be among the most common commercially others are available which are intended predominantly for housing instruments having different diameters, without the necessity of interchanging the second obturator. Advantageously, the instrument according to this disclosure is suitable for housing, via an appropriate adaptor, any commercial sealing system.

As those skilled in the art will also appreciate, tubular body 1 of the expandable anchor guide, according to this disclosure, can be made in a different number of cylindrical sectors 1a than the three sectors described and illustrated here, giving consideration to the purpose for which the anchor guide is intended. Thus, it is now possible to better approximate the circular shape of the opening realized, while taking into account the increasing cost of the instrument.

Various modifications and alterations may be appreciated based on a review of this disclosure. These changes and additions are intended to be within the scope and spirit of the disclosure as in defined by the following claims.

What is claimed is:

1. An anchor guide for a trocar for use in laparoscopic surgery, the guide comprising a tubular body with a member for its anchorage to an access hole for entering a body cavity, wherein the tubular body is formed by a plurality of substantially circular sectors, said sectors being rigid along a circumferential direction of the tubular body and moveable radially toward and away from a longitudinal axis of the body between a first position, where they flank one another according to a substantially circular first arrangement of diameter generally equal to that of the tubular body, and a second position, at which they are generally equidistant from one another according to a substantially circular second arrangement of greater diameter than that of the first circular arrangement, the plurality of sectors being rotatably connected to a support element and a manual operation member, moveably connected to the support element, being further provided for moving the sectors from the first to the second position and vice versa.

2. The anchor guide set forth in claim 1, wherein the anchor member comprises a saw tooth thread formed along an outer surface of the tubular body.

3. The anchor guide set forth in claim 1, wherein a tube can be attached within the tubular body in open condition, the tube having two elastic disc-shaped membranes extending from its ends and foldable within it.

4. The anchor guide set forth in claim 1, further comprising a valve having a fixed support reversibly connectable to the manual operation member, a control ring nut rotatably engaged within the fixed support and an elastic membrane obturator having a toroidal shape, at rest, with an "omega" cross section, tightened to the inner walls of the control ring nut and the fixed support, whereby, upon rotating the control ring nut relative to the support, the elastic membrane is subjected to torsion, causing it to close radially like a diaphragm, wherein the control ring nut is maintained in a desired angular position by flexible arms extending axially from the fixed support, the arms having inner radial projections for engagement with axial grooves on the edge of the control ring nut.

5. The anchor guide set forth in claim 1, wherein the moveable ring nut includes a fastener for a valve body.

6. The anchor guide set forth in claim 5, wherein the valve body comprises a fixed support reversibly connected to the moveable ring nut and a control ring nut pivotally engaged with the fixed support and maintained in a desired angular position by flexible arms extending axially from the fixed support, the arms having inner radial projections for engagement with axial grooves formed on the edge of the control ring nut.

7. The anchor guide set forth in claim 1, wherein each of the substantially circular sectors has an arm extending therefrom in a substantially tangential manner, each arm having an end mounted to one of the respective circular sectors and a free end, the free end being hinged to the support element, the operation member acting on the arms.

8. The anchor guide set forth in claim 7, wherein the arms are housed generally coplanarly within and relative to the annular body.

9. The anchor guide set forth in claim 7, wherein the arms have a curved profile.

10. The anchor guide set forth in claim 7, wherein the support element is an annular body and the manual operation member comprises a moveable ring nut rotating coaxially on the annular body and thrust pins extending orthogonally from the moveable ring nut and arranged so as to interfere with the arms during movement of the ring nut, the sliding of the thrust pins along the arms effecting their angular displacement.

11. The anchor guide set forth in claim 10, wherein the manual operation member further comprises closure pins extending from the moveable ring nut and also adapted to interfere with the arms from an opposing portion of the thrust pins.

12. The anchor guide set forth in claim 10, wherein the arms are hinged to the support element through pins passing respectively therethrough and engaged with respective circumferential slots formed along the moveable ring nut, reversible tightening members of the pins abutting the moveable ring.

* * * * *